United States Patent [19]

Rand

[11] Patent Number: 4,841,970
[45] Date of Patent: Jun. 27, 1989

[54] CRYOGENIC RECTAL INSERT

[76] Inventor: Herbert Rand, 5425 NW. 82 Ave., Miami, Fla. 33166

[21] Appl. No.: 148,549

[22] Filed: Jan. 26, 1988

[51] Int. Cl.⁴ .............................................. A61F 7/12
[52] U.S. Cl. .................................. 128/401; 128/403; 128/303.12
[58] Field of Search .............................. 128/399–403, 128/774, 778, 782, 742, 303.12, 303.1; 604/113–114

[56] References Cited

U.S. PATENT DOCUMENTS

| | | | |
|---|---|---|---|
| 2,541,520 | 2/1951 | Kegel | 128/778 |
| 2,825,339 | 3/1958 | McGee | 128/403 |
| 3,939,842 | 2/1976 | Harris | 128/401 |
| 4,216,783 | 8/1980 | Kaiser et al. | 128/748 X |
| 4,331,151 | 5/1982 | Golden | 128/401 |
| 4,563,182 | 1/1986 | Stoy et al. | 128/401 X |
| 4,638,806 | 1/1987 | Bartlett | 128/401 X |

*Primary Examiner*—Kyle L. Howell
*Assistant Examiner*—Angela D. Sykes

[57] ABSTRACT

A cryogenic proctologic insert for treating hemorrhoids by lowering the surface temperature of the affected portion of the rectal canal. The insert is formed of a tubular plastic portion filled with a congealable fluid. Extended heat transfer surfaces are provided in the interior of the insert to promote heat transfer to and from the fluid.

6 Claims, 1 Drawing Sheet

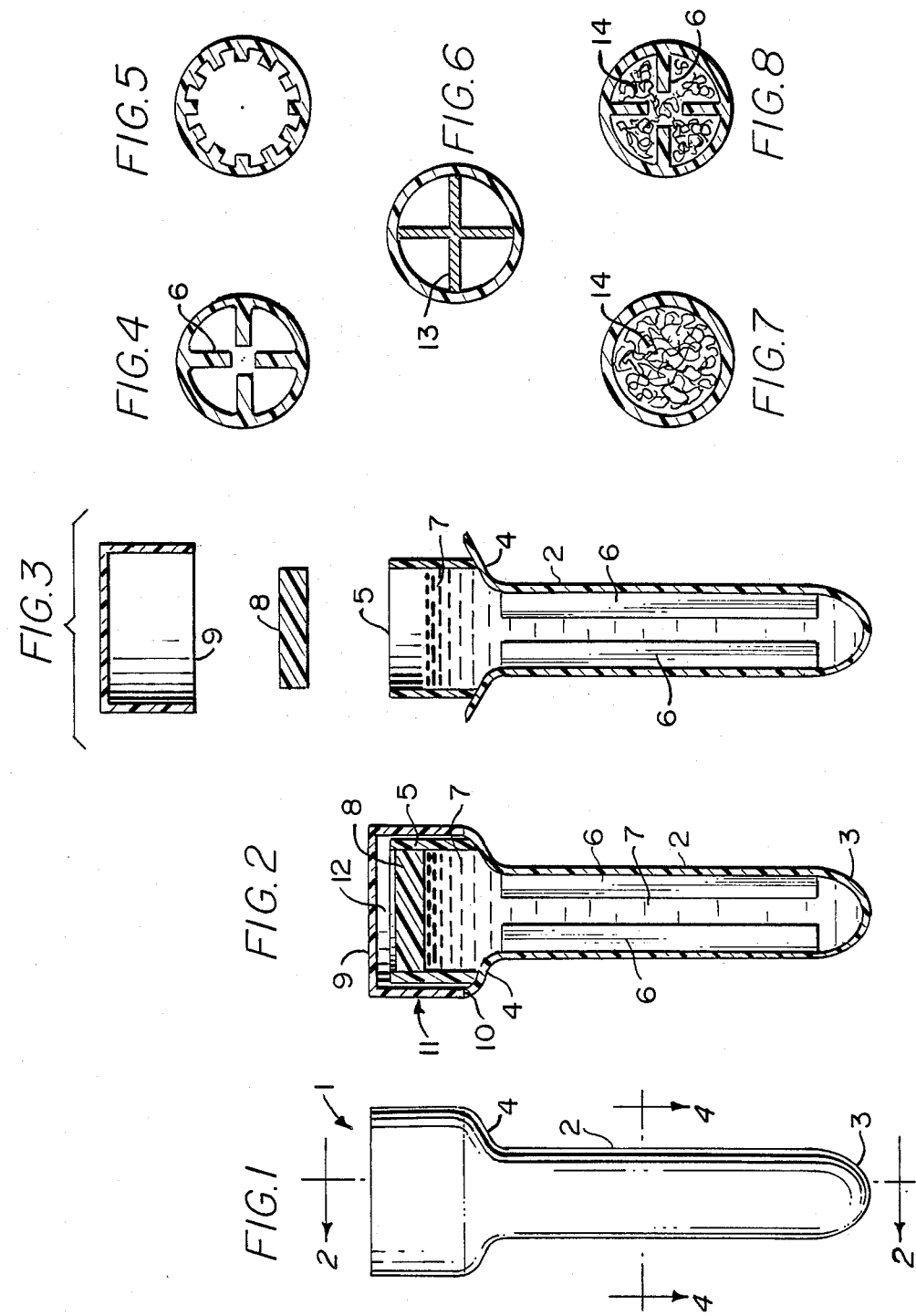

CRYOGENIC RECTAL INSERT

BACKGROUND OF THE INVENTION

This invention relates to a plastic cryogenic device that is used rectally for the relief of piles and hemorrhoids and the symptoms that accompany this malady or disorder.

Piles or hemorrhoids are swollen varicose veins in the anal canal that may or may not have extruded beyond the anus. This condition is painful during bowel elimination. Bleeding from and itching in the area are also common occurrences. Hemorrhoids are prevalent in adults over thirty years of age and especially so in women during the last trimester of pregnancy. Cold compresses have long been used for temporary relief to reduce swelling and control bleeding. Cold has long been recognized as a means of reducing swelling and with a greater degree of cold, known as cryogenics, a total aesthetic effect may be accomplished. Cryoplexy is commonly used in eye surgery as is ethyl chloride for a local anesthetic. It is therefore reasonable to assume that controlled cold therapy would be beneficial for treating the various symptoms related to piles and hemorrhoids. This form of treatment has been enhanced by the new medically approved plastics available with the newer fabricating methods such as injection molding. These improvements allow a feasible cryogenic device with a freezeable liquid contained within the insertable portion for the relief of the symptoms associated with piles and hemorrhoids.

Harris in U.S. Pat. No. 3,939,842 dated Feb. 24, 1976 describes a polyethylene container of a size and shape suitable for insertion in the rectal canal. The container is filled with a congealable fluid such as water, ethylene glycol or propylene glycol and hermetically sealed. To use the device, the rectal insert is first placed in the freezer compartment of the refrigerator for a time sufficient to cause the liquid to congeal. The device is then inserted into the rectum with a suitable water soluble lubricant such as KY jelly. The cold temperature is released gradually towards the swollen tissues and accompanying vascularity. After the insert has attained body temperature, it is removed and discarded.

This invention relates to an improved cryogenic rectal device where heat transfer is accomplished through the congealable fluid by means of the extended heat transfer system provided by the longitudinal fins within the cylinder of the insert. The effectiveness and efficiency of the cryotherapy treatment is thereby improved. The device is also capable of being reused.

SUMMARY OF THE INVENTION

A rectal device is formed of a plastic material, such as polyethylene which is nonreactive to body tissues. A hollow stem portion (cylinder) is formed to accept a measured amount of a congealable liquid. Extending the length of the stem portion, are a number of integral fins which aid in transferring heat from the outer surface of the insert. As an alternative, the aforementioned fins may comprise a separate insertable fin structure or a heat conductive wire mesh acting alone or in combination with the longitudinal fin structure. After filling the stem portion with a congealable liquid, the open end is hermetically sealed by means of an enlarged cap structure. This cap may also be construed as the handle or the portion that is handled during insertion and the means of removal after treatment.

DESCRIPTION OF THE DRAWINGS

FIG. 1 is a plan view of the rectal insert.

FIG. 2 is a cross-sectional view of the rectal insert taken along lines 2—2 of FIG. 1.

FIG. 3 is an exploded view showing the various parts before assembly.

FIG. 4 is an enlarged cross-sectional view taken along lines 4—4 of FIG. 1 showing the heat transfer fins.

FIG. 5 is an enlarged cross-sectional view taken along lines 4—4 of FIG. 1 showing a modified fin structure.

FIG. 6 is an enlarged cross-sectional view taken along lines 4—4 of FIG. 1 showing another modified fin structure.

FIG. 7 is an enlarged cross-sectional view taken on lines 4—4 of FIG. 1 showing an alternate heat transfer structure employing a wire mesh.

FIG. 8 is an enlarged cross-sectional view taken on line 4—4 of FIG. 1 showing a combination of the FIG. 4 and FIG. 7 constructions.

DESCRIPTION OF THE PREFERRED EMBODIMENTS

Referring now in detail to the drawings, FIGS. 1 and 2 show a rectal insert 1 for the cryogenic treatment of hemorrhoids. The insert is formed of suitable plastic materials which are approved for medical use by FDA.

The insert 1 has a cylindrical portion 2 about ½ inch in diameter and about 3 inches long. The wall thickness is approximately 1–5 mils. The above, as well as all other dimensions given are not critical and subject to variations depending upon the material used and method of fabrication. One end of cylindrical portion 2 is provided with a bullet-shaped end 3 to facilitate insertion into the rectal canal. The other end of the cylindrical portion is provided with an outwardly flared section 4.

As can best be seen in FIGS. 2 and 3, a cylindrical collar 5 is integrally attached to the flared section 4 at a location spaced slightly inwardly from the outer periphery of the flared section. The cylindrical collar 5 may be bonded to the flared section 4 by means of one of the many bonding techniques known in the plastic fabrication arts. Alternatively, the cylindrial collar may be formed along with the cylindrical portion 2 in a one-step molding operation. The cylindrical collar 5 has an approximate length of 0.875 inches.

Extending inwardly from the inner surface of the cylindrical portion 2 are a plurality of integral heat conductive fins 6. Even though formed of plastic which is a relatively poor conductor as compared to metal, the fins do supply extended heat transfer surfaces to conduct heat to and from the surrounding congealable fluid 7 contained within the cylindrical portion 2. The integrally extending fin structure is also shown in FIG. 4 which is a cross-sectional view taken on line 4—4 of FIG. 1.

Viewing FIG. 3, assembly of the rectal insert is completed by inserting a suitable plug 8 of cork or resilient plastic into cylindrical collar 5 to confine the congealable fluid as shown in FIG. 2. A cup member 9 of a length and inside diameter to provide a slip fit over cylindrical collar 5 with a slight clearance 12 at the top is placed over the cylindrical collar and bottomed against the outer periphery of flared section 4. The bottom of cup member 9 is sealed around the outer periphery of flared section 4 to form a hermetic seal at 10. The seal is made perfectly smooth and round without any crevices which may harbor bacteria.

The cylindrical collar 5 and cup member 9 form a cylindrical cap 11 which (1) hermetically seals the congealable fluid, (2) serves as a reservoir for the fluid, and (3) primarily acts as a stop to limit rectal insertion.

The congealable fluid may, for example, be water, propylene glycol, or mixtures thereof. The important requirements are a relatively high latent heat of fusion and a freezing temperature below 32 degrees F.

The slight clearance 12 between the top of plug 8 and the closure wall of cup member 9 is provided to allow for expansion of the congealable liquid when freezing.

FIG. 5 shows a modified fin structure. Instead of 4 radially extending fins which penetrate almost to the center of cylindrical portion 2 a large number of smaller radial fins are arranged to extend only part way into the interior.

FIG. 6 shows a modified fin structure wherein a metallic crossed fin structure 13 is employed. The crossed fin structure has an outside diameter to snugly engage the smooth interior bore of cylindrical portion 2. The excellent thermal conductivity of the metal fins greatly accelerates the freezing and melting rates of the congealable fluid.

FIG. 7 shows a modification wherein the cylindrical portion is filled with a conductive wire mesh 14 for greatly accelerating the freezing and melting rates of the congealable fluid.

FIG. 8 shows a modification wherein the integral fin structure 6 of FIG. 4 is combined with wire mesh 14.

Before use, the rectal insert is placed in the freezer compartment of the refrigerator where the congealable liquid freezes. Depending upon the freezer temperature, freezing time should be between 1 to 2 hours. The outer cylindrical portion is then coated with some water soluble lubricant formulated for use in body cavities. The insert is then inserted into the rectum with the cup member 9 acting as a stop. After about 3–10 minutes, the rectal insert will begin to approach body temperature and the treatment is completed. The insert is then removed and washed in soap and water or any suitable disinfectant to be used again. It may be stored in the freezer for later use as needed.

What is claimed is:

1. A cryogenic rectal insert for the treatment of hemorrhoids comprising a plastic substantially cylindrical portion of a length and diameter suitable for insertion in the rectal canal of the body, one end of said cylindrical portion being bullet-shaped to facilitate rectal insertion, the other end of said cylindrical portion being outwardly flared, a congealable fluid filling said cylindrical portion, a cylindrical cap joined to an outer perimeter portion of said flared end for hermetically sealing said congealable fluid in said cylindrical portion and for forming an enlargement limiting rectal insertion; and means in contact with the internal surface of said cylindrical portion and extending into said congealable fluid to promote heat transfer into and out of said congealable fluid.

2. The cryogenic rectal insert in accordance with claim 1 wherein said means in contact with the internal surface of said cylindrical portion and extending into said congealable fluid to promote heat transfer comprises a radially extending integral fin structure.

3. The cryogenic rectal insert in accordance with claim 1 wherein said means in contact with the internal surface of said cylindrical portion and extending into said congealable fluid to promote heat transfer comprises an insertable heat conductive fin structure.

4. The cryogenic rectal insert in accordance with claim 1 wherein said means in contact with the internal surface of said cylindrical portion and extending into said congealable fluid to promote heat transfer comprises a heat conductive wire mesh.

5. The cryogenic rectal insert in accordance with claim 2 wherein a heat conductive wire mesh is provided between the spaces defined by the radially extending integral fin structure.

6. The cryogenic rectal insert in accordance with claim 1 wherein said cylindrical cap comprises a cylindrical collar joined to an outer portion of said flared end, a plug mounted within said cylindrical collar to confine said congealable fluid, and a cup member fitting over said cylindrical collar and joined to said outer perimeter portion of said flared end to form a hermetically sealed unit.

* * * * *